(12) United States Patent
Kim et al.

(10) Patent No.: US 7,702,384 B2
(45) Date of Patent: Apr. 20, 2010

(54) ZONELESS TACHYARRHYTHMIA DETECTION WITH REAL-TIME RHYTHM MONITORING

(75) Inventors: Jaeho Kim, Redmond, WA (US); Joseph M. Bocek, Seattle, WA (US); Karl Stoklosa, St. Paul, MN (US); Scott Walczak, Eden Prairie, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1025 days.

(21) Appl. No.: 11/301,716

(22) Filed: Dec. 13, 2005

(65) Prior Publication Data

US 2007/0135848 A1 Jun. 14, 2007

(51) Int. Cl.
*A61B 5/04* (2006.01)
(52) U.S. Cl. ........................................ 600/518; 607/14
(58) Field of Classification Search ................. 600/509, 600/510, 513, 515, 516, 518, 523, 300, 508, 600/517; 607/4, 5, 9, 14; 324/378; 361/517; 429/90; 438/800; 439/722, 885; 604/508, 604/96.01; 606/15
See application file for complete search history.

(56) References Cited

U.S. PATENT DOCUMENTS

| | | | | |
|---|---|---|---|---|
| 4,583,533 A * | 4/1986 | Goodley et al. | ................ | 602/36 |
| 5,063,928 A * | 11/1991 | Grevis et al. | ................ | 607/14 |
| 5,251,621 A * | 10/1993 | Collins | ................ | 607/4 |
| 5,327,900 A | 7/1994 | Mason et al. | | |
| 5,379,776 A | 1/1995 | Murphy et al. | | |
| 5,458,620 A * | 10/1995 | Adams et al. | ................ | 607/5 |
| 5,462,060 A | 10/1995 | Jacobson et al. | | |
| 5,891,170 A | 4/1999 | Nitzsche et al. | | |
| 5,978,707 A * | 11/1999 | Krig et al. | ................ | 607/14 |
| 6,076,014 A | 6/2000 | Alt | | |
| 6,190,324 B1 | 2/2001 | Kieval et al. | | |
| 6,611,713 B2 * | 8/2003 | Schauerte | ................ | 607/14 |
| 6,636,764 B1 | 10/2003 | Fain et al. | | |
| 7,139,607 B1 * | 11/2006 | Shelchuk | ................ | 607/9 |
| 7,328,063 B2 | 2/2008 | Zhang et al. | | |
| 2003/0060849 A1 | 3/2003 | Hsu | | |
| 2004/0088013 A1 | 5/2004 | Stadler et al. | | |
| 2004/0093035 A1 | 5/2004 | Schwartz et al. | | |
| 2006/0217621 A1 | 9/2006 | Kim et al. | | |
| 2007/0197928 A1 | 8/2007 | Kim et al. | | |

OTHER PUBLICATIONS

Chiang et al. Median Filtering as a Sudden Onset Criterion to Separate Sinus Tachycardia from Ventricular Tachycardia. Proceedings of Computers in Cardiology. 1992:379-382.*

(Continued)

*Primary Examiner*—Carl H Layno
*Assistant Examiner*—Jeremiah T Kimball
(74) *Attorney, Agent, or Firm*—Schwegman, Lundberg & Woessner, P.A.

(57) ABSTRACT

A system including an implantable medical device (IMD). The IMD includes a ventricular contraction sensing circuit that provides a sensed ventricular contraction signal, a timer circuit that provides a ventricular time interval between ventricular contractions, and a controller circuit coupled to the timer circuit, the controller circuit determines the ventricular contraction rate using the ventricular time interval. The controller circuit further includes a tachyarrhythmia detection module that declares tachyarrhythmia, in response to detecting a sudden rate increase, without comparing a ventricular rate or time interval to a respective tachyarrhythmia detection rate or time interval threshold.

33 Claims, 8 Drawing Sheets

OTHER PUBLICATIONS

"U.S. Appl. No. 11/276,213, Restriction Requirement mailed Feb. 27, 2009", 7 pgs.

"U.S. Appl. No. 11/276,213, Non Final Office Action mailed May 6, 2009", 10 pgs.

Bansch, D., et al., "The 1+1 trial: a prospective trial of a dual- versus a single-chamber implantable defibrillator in patients with slow ventricular tachycardias.", *Circulation*, 110(9), (Aug. 31, 2004), 1022-9.

* cited by examiner

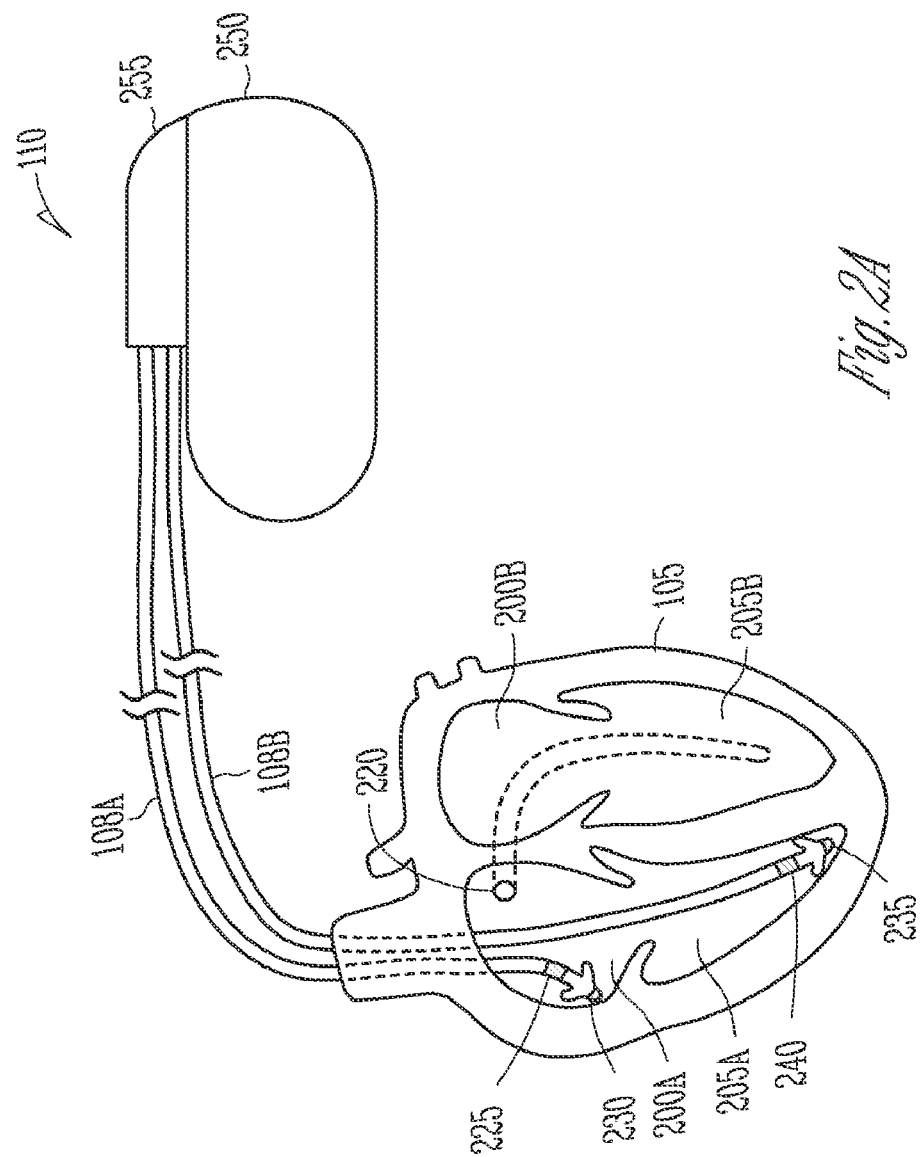

ZONELESS TACHYARRHYTHMIA DETECTION WITH REAL-TIME RHYTHM MONITORING

TECHNICAL FIELD

The field generally relates to implantable medical devices and, in particular, but not by way of limitation, to systems and methods for detecting tachyarrhythmia in a patient.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), cardiac resynchronization therapy devices, and devices that include a combination of such capabilities. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events include heart chamber expansions or contractions. By monitoring cardiac signals indicative of expansions or contractions, IMDs are able to detect tachyarrhythmia. IMDs are further able to provide therapy for tachyarrhythmia, such as high energy shock therapy or anti-tachycardia pacing (ATP). Tachyarrhythmia includes abnormally rapid heart rate, or tachycardia, including ventricular tachycardia (VT) and supraventricular tachycardia. Tachyarrhythmia also includes rapid and irregular heart rate, or fibrillation, including ventricular fibrillation (VF). Typically, ICDs detect tachyarrhythmia by first detecting a rapid heart rate. Other detection methods in addition to fast rate detection are used to reduce the incidence of inappropriate shocks. The present inventors have recognized a need for improved sensing of events related to device recognition of tachyarrhythmia.

SUMMARY

This document discusses, among other things, systems and methods for detecting events related to cardiac activity. A system example includes an implantable medical device (IMD). The IMD includes a ventricular contraction sensing circuit that provides a sensed ventricular contraction signal, a timer circuit that provides a ventricular time interval between ventricular contractions, and a controller circuit coupled to the timer circuit, the controller circuit determines the ventricular contraction rate using the ventricular time interval. The controller circuit further includes a tachyarrhythmia detection module that declares tachyarrhythmia, in response to detecting a sudden rate increase, without comparing a ventricular rate or time interval to a respective tachyarrhythmia detection rate or time interval threshold.

A method example includes using an IMD to monitor ventricular contraction intervals (V-V intervals) of a subject, detect a sudden rate increase in the V-V intervals, determine that the sudden rate increase is sustained for a specified period of time, and deem the sudden rate increase indicative of tachyarrhythmia.

Another method example includes monitoring a ventricular contraction rate of a subject, monitoring an atrial contraction rate of the subject, and declaring tachyarrhythmia if the ventricular contraction rate exceeds the atrial contraction rate.

This summary is intended to provide an overview of certain subject matter of the present patent application. It is not intended to provide an exclusive or exhaustive explanation of the invention. The detailed description is included to provide further information about the subject matter of the present patent application.

BRIEF DESCRIPTION OF THE DRAWINGS

FIGS. 2A-B illustrate implantable medical devices coupled by one or more leads to a heart.

DETAILED DESCRIPTION

In the following detailed description, reference is made to the accompanying drawings which form a part hereof, and specific examples in which the invention may be practiced are shown by way of illustration. It is to be understood that other examples may be used and structural or logical changes may be made without departing from the scope of the present invention.

This document discusses systems and methods for improved detection of cardiac events. Because it is assumed that tachyarrhythmia is accompanied by fast heart rates, implantable medical devices (IMDs), such as implantable cardioverter defibrillators (ICDs) for example, typically detect tachyarrhythmia when a heart rate suddenly exceeds a specified threshold heart rate. The term specified refers to a parameter being a hard-set fixed value as well as being a programmable parameter whose value is set with a device programmer. If a patient experiences tachyarrhythmia at a heart rate below the specified threshold heart rate or below typical cutoff rates for detection (i.e., a slow tachyarrhythmia), the tachyarrhythmia is not detected and treatment is therefore not provided. Some patients that have an implantable cardiac function management (CFM) device may experience episodes of slow tachyarrhythmia more frequently over time after an ICD is implanted. The present inventors have recognized a need to detect slow tachyarrhythmia. The present inventors have also recognized a need to provide a warning system to identify when a patient is experiencing slow tachyarrhythmia and to notify a caregiver.

Typically, ICDs divide the spectrum of possible heart rates into zones. For example, if an ICD detects that a heart rate falls within a zone that defines ventricular tachycardia, the ICD may then trigger other detection methods to confirm that a patient is indeed experiencing ventricular tachycardia. Detecting tachyarrhythmia without relying on these heart rate zones allows an IMD to detect tachyarrhythmia at slower heart rates than a specified heart rate.

Some CFMs include sensors that determine whether to increase or decrease a pacing rate. These devices often have a maximum sensor rate (MSR) that is the maximum rate at which the device is allowed to pace the heart in response to the output of the sensor. Also, these devices often have a maximum tracking rate (MTR) that is the maximum rate at which the device is allowed pace the ventricle to maintain tracking with the atrium. The greater of the MSR and MTR represents the maximum pacing rate of the device. This rate is typically set below the tachyarrhythmia heart rate zones in order to avoid pacing the patient into such zones. Detecting tachyarrhythmia without using heart rate zones allows an IMD to detect tachyarrhythmia at rates below the maximum pace rate.

Figure 1:
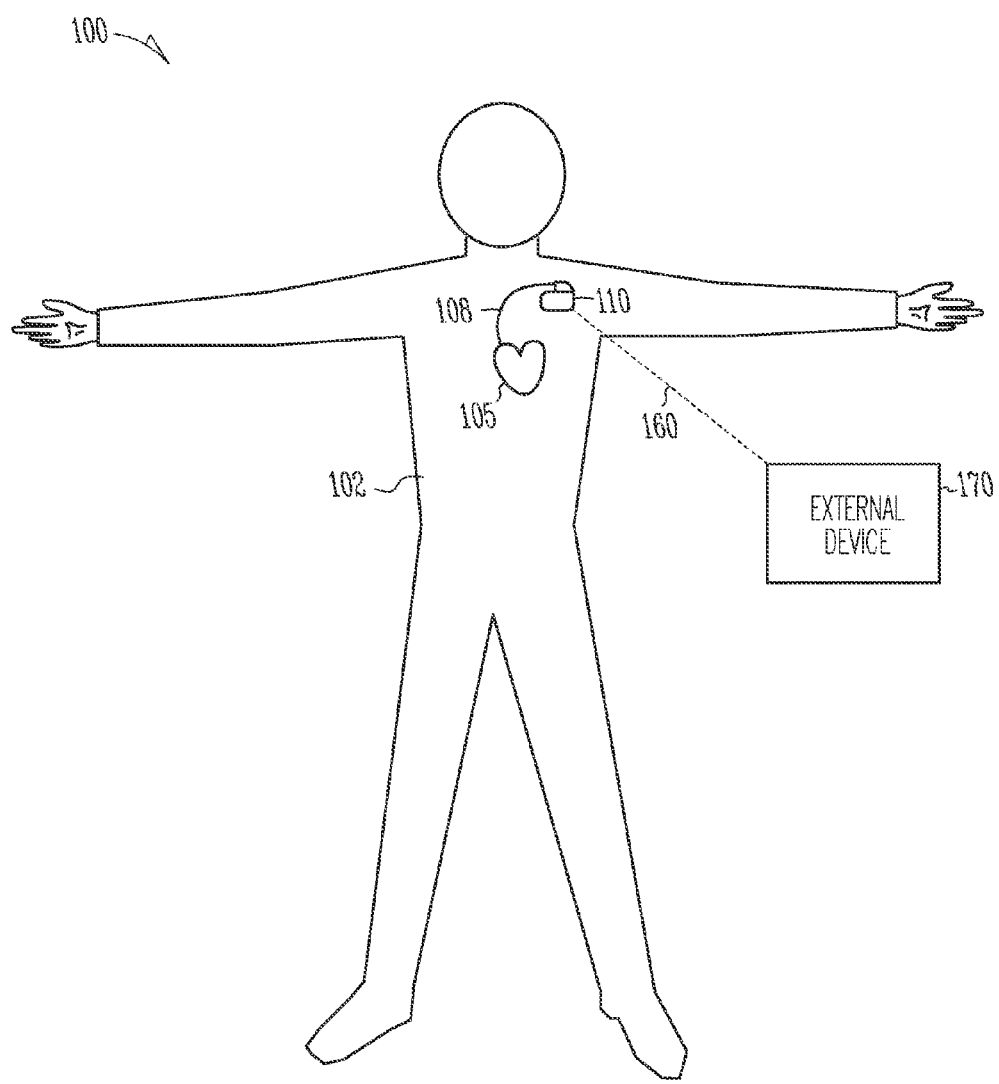
FIG. 1 illustrates an example of portions of a system that uses an implantable medical device.

FIG. 1 illustrates an example of portions of a system 100 that uses an implantable medical device (IMD) 110. The system 100 shown is used to treat a cardiac arrhythmia. The IMD 110 includes an electronics unit coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by electrical contacts called "electrodes" to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing electrical activity of the heart 105, including electrical activity related to contractions of the atria or ventricles.

Figure 2B:
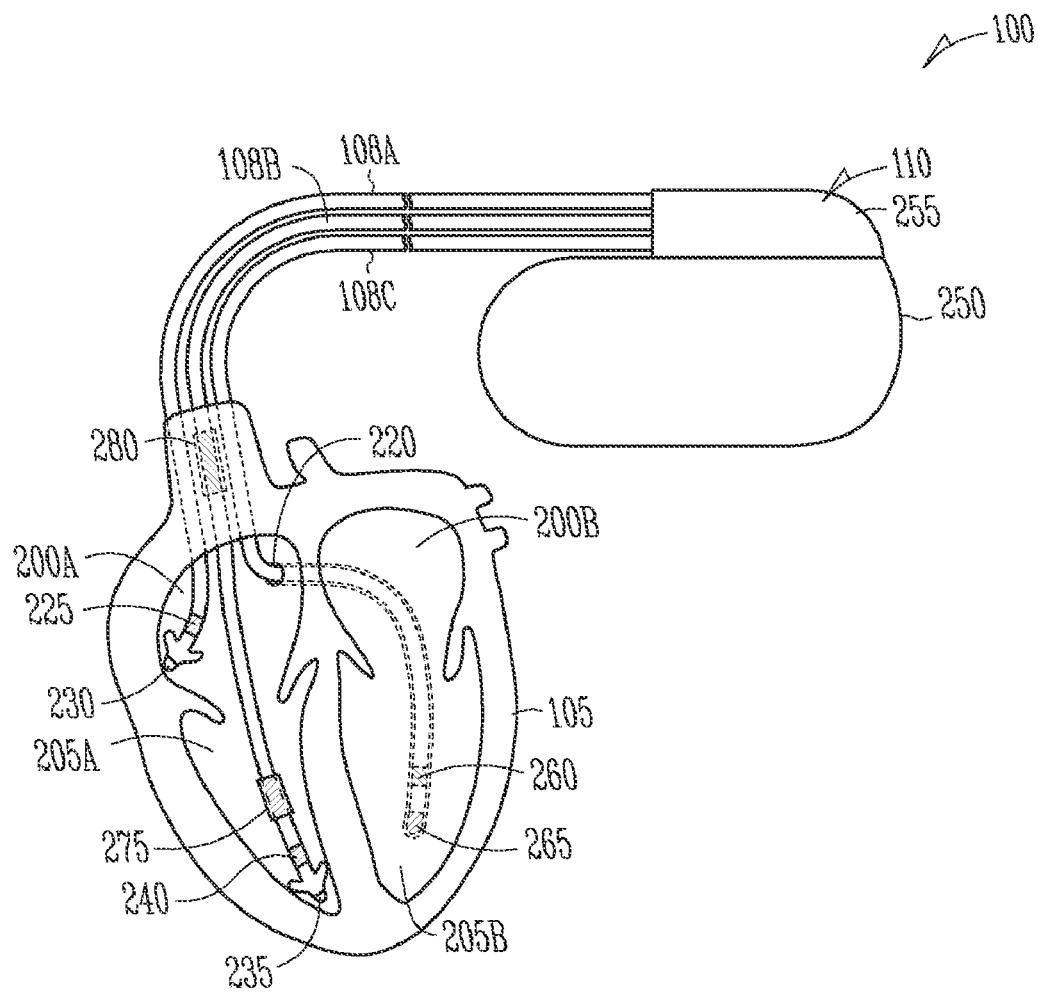

FIGS. 2A-B illustrate IMDs 110 coupled by one or more leads 108A-C to heart 105. Heart 105 includes a right atrium 200A, a left atrium 200B, a right ventricle 205A, a left ventricle 205B, and a coronary sinus 220 extending from right atrium 200A. In the example in FIG. 2A, atrial lead 108A includes electrodes (electrical contacts, such as ring electrode 225 and tip electrode 230) disposed in an atrium 200A of heart 105 for sensing signals, or delivering pacing therapy, or both, to the atrium 200A.

Ventricular lead 108B includes one or more electrodes, such as tip electrode 235 and ring electrode 240, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. The example in FIG. 2B includes a third cardiac lead 108C attached to the IMD 110 through the header 255. The third lead 108C includes ring electrodes 260 and 265 placed in a coronary vein lying epicardially on the left ventricle (LV) 205B via the coronary vein 220.

In the example of FIG. 2B, lead 108B further includes a first defibrillation coil electrode 275 located proximal to tip and ring electrodes 235, 240 for placement in a right ventricle (RV), and a second defibrillation coil electrode 280 for placement in the superior vena cava (SVC) located proximal to the first defibrillation coil 275, tip electrode 235, and ring electrode 240. In some examples, high energy shock therapy is delivered from the first or RV coil 275 to the second or SVC coil 280. In some examples, the SVC coil 280 is electrically tied to an electrode formed on the IMD can 250. This improves defibrillation by delivering current from the RV coil 275 more uniformly over the ventricular myocardium. In some examples, the therapy is delivered from the RV coil 275 only to the electrode formed on the IMD can 250.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes.

Figure 3A:
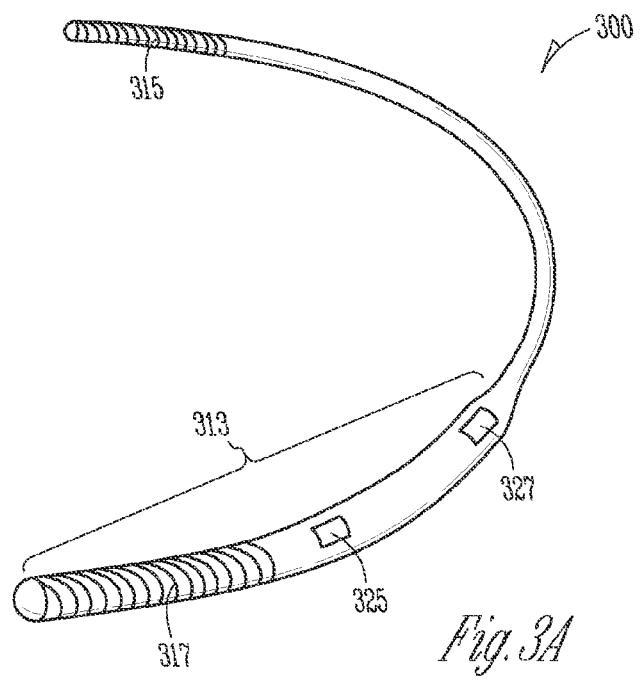
FIGS. 3A-B illustrate an implantable medical device that does not use intravascular leads.
Figure 3B:
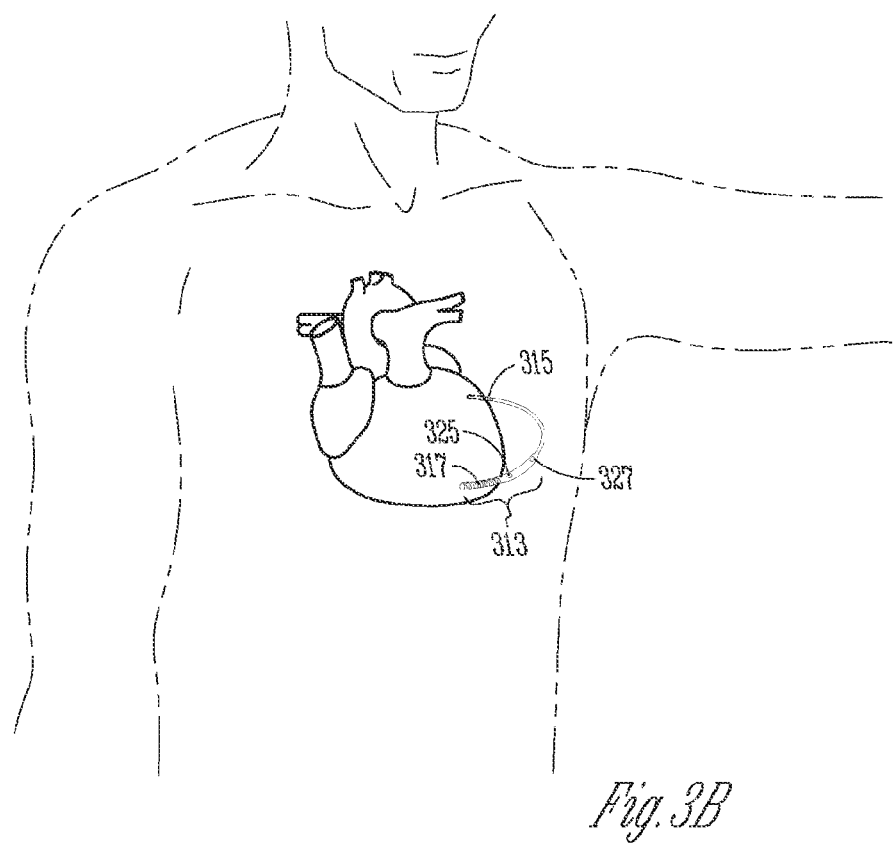

FIGS. 3A-B show an example of an IMD 300 that does not use intravascular leads to sense cardiac signals. FIG. 3A shows that the IMD 300 includes a thicker end 313 to hold the power source and circuits. The IMD 300 also includes electrodes 325 and 327 for remote sensing of cardiac signals. Cardioversion/defibrillation is provided through electrodes 315 and 317. FIG. 3B shows the positioning of the IMD 300 within a patient.

Figure 4:
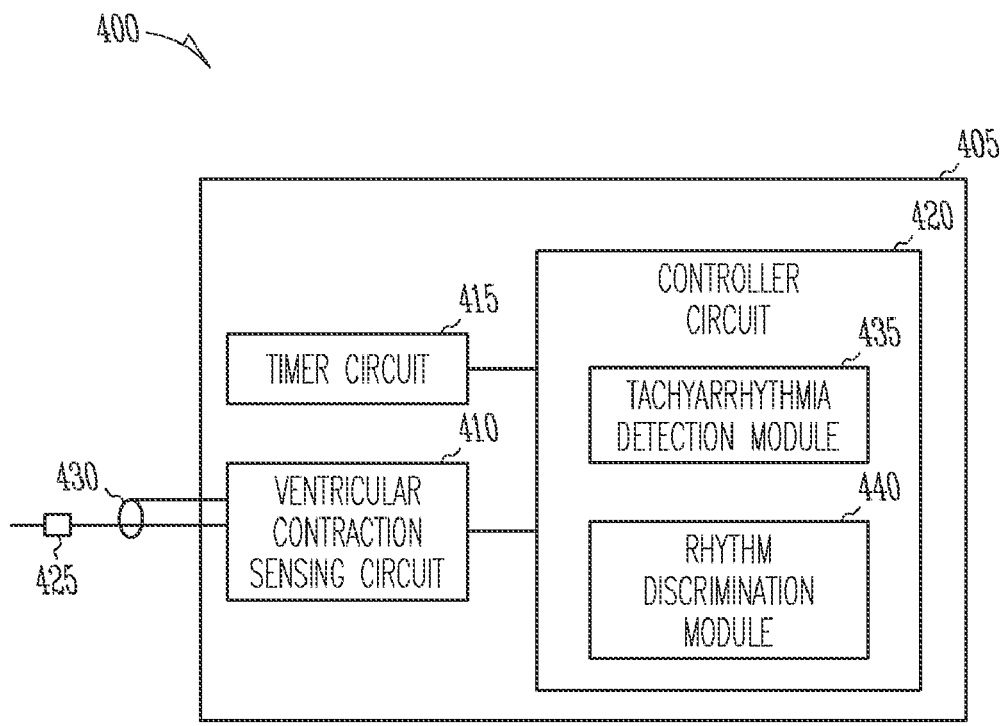
FIG. 4 shows an example of portions of a system that detects tachyarrhythmia.

FIG. 4 shows an example of a system 400 that detects tachyarrhythmia, including detecting tachyarrhythmia at rates below typical tachyarrhythmia detection cutoff rates. The system 400 includes an IMD 405, which in turn includes a ventricular contraction sensing circuit 410, a timer circuit 415, and a controller circuit 420. The ventricular contraction sensing circuit 410 provides a sensed ventricular contraction signal. In the example shown, the signal is sensed between lead tip electrode 425 and lead ring electrode 430. In some examples the signal is sensed between one lead electrode and a shock electrode placed in the right ventricle (RV). The timer circuit 415 is operable to provide a ventricular time interval between contractions of a ventricle or ventricles. The controller circuit 420 is coupled to the timer circuit 415 and is operable to determine the ventricular contraction rate using the sensed ventricular contraction signal and the ventricular time interval, such as by executing an algorithm or algorithms implemented by hardware, software, firmware or any combination of hardware, software or firmware.

The controller circuit 420 further includes a tachyarrhythmia detection module 435 that declares tachyarrhythmia when detecting a sudden rate increase. A sudden rate increase is typically represented by a specified number of consecutive accelerated beats. The number can be specified by being a hard fixed number or by being a programmable number programmed with a device programmer. As an illustrative example, a sudden rate increase is defined as three consecutive accelerated beats. In another example, a sudden rate increase is defined as six consecutive accelerated beats. An accelerated beat is declared by some criterion other than a comparison to a fixed tachyarrhythmia rate threshold (i.e., without a comparison to one or more tachyarrhythmia heart rate zones or one or more tachyarrhythmia detection cutoff heart rates). In some examples, an accelerated beat is identified when a difference between a last average ventricular contraction interval (V-V interval) and the current V-V interval is greater than a specified percentage of the last average V-V interval. As an illustrative example, an accelerated beat is identified when the difference between the last average V-V interval and the current V-V interval is greater than ten percent (10%) of the last average V-V interval, i.e., $$VV_{AVG}(n-1) - VV(n) > (0.1) * (VV_{AVG}(n-1)),$$

where $VV_{AVG}(n-1)$ is the last or previous average V-V interval and $VV(n)$ is the current V-V interval. If a current beat is not an accelerated beat, the current V-V interval will be close to the average interval and the difference will be close to zero. If the current beat is an accelerated beat, the current V-V interval will be smaller than the average interval value and the difference will increase to a quantity larger than zero. As the current V-V interval decreases, eventually the difference will exceed the specified percentage difference and the tachyarrhythmia detection module 435 identifies the beat as an accelerated beat.

Figure 5:
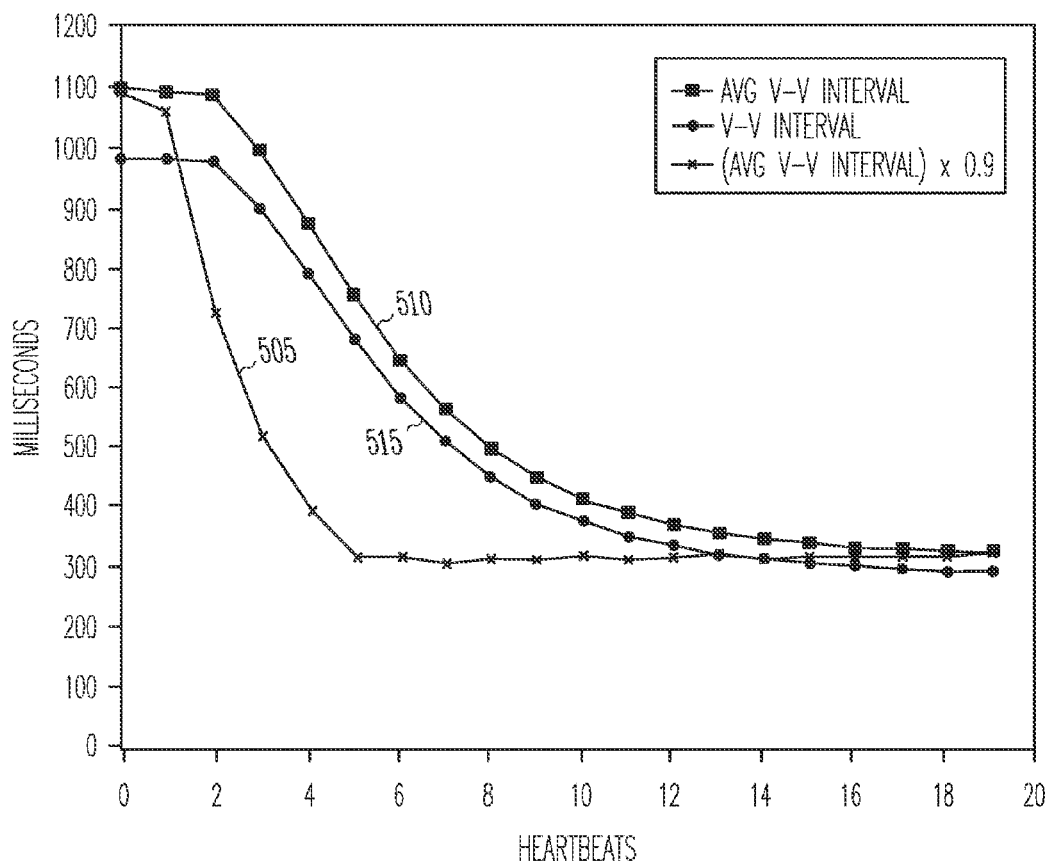
FIG. 5 illustrates graphs of ventricular-contraction intervals.

There is a complication in calculating accelerated beats. If the accelerated beat intervals are included in the calculation of the average V-V interval, the accelerated beats will skew the average to faster intervals or a fast interval steady state if the sudden rate increase is sustained. This is illustrated in FIG. 5. An onset of accelerated beats that are sustained is shown by graph 505. Graph 510 shows the effect on the average V-V interval. Graph 515 shows 0.9*(average V-V interval). It can be seen in the graphs that the fast V-V intervals and the average V-V interval converge, making it difficult for subsequent accelerated beats to be detected. In some examples, this complication is overcome by the controller circuit 420 not including the accelerated beats in the calculation of the average V-V interval. In another example, any accelerated beat that occurs after a specified number of accelerated beats, such as three accelerated beats for example, is not used to update the average V-V interval.

In another example, the controller circuit 420 calculates a temporary average V-V interval, different from the last average V-V interval, using the number of consecutive accelerated beats until a sudden rate increase is defined. The temporary average V-V interval is not updated like the normal average V-V interval and is used to identify an accelerated beat after the average V-V interval converges to fast V-V intervals. For example, when an initial sudden rate increase is declared, such as after detecting a third consecutive accelerated beat, the average V-V interval is updated but becomes a temporary average V-V interval. The normal average V-V interval is preserved. Any V-V interval shorter than the temporary V-V interval is deemed to be an accelerated beat.

In some examples, the IMD 405 includes an atrial contraction sensing circuit configured to sense a cardiac signal of an atrium of the heart. The controller circuit 420 monitors the ventricular and atrial contraction rate and the tachyarrhythmia detection module 435 declares tachyarrhythmia when the ventricular contraction rate exceeds the atrial contraction rate by a specified rate difference threshold. As an illustrative example, the tachyarrhythmia detection module 435 declares tachyarrhythmia when the ventricular contraction rate exceeds the atrial contraction rate by ten beats per minute (bpm). In some examples, the tachyarrhythmia detection module 435 declares tachyarrhythmia when either the ventricular contraction rate exceeds the atrial contraction rate or when a sudden rate increase is detected. In some examples, the tachyarrhythmia detection module 435 declares tachyarrhythmia when both the ventricular contraction rate exceeds the atrial contraction rate and a sudden rate increase is detected.

In some examples, the controller circuit 420 includes a rhythm discrimination module 440 that discriminates between ventricular tachyarrhythmia (such as ventricular tachycardia (VT), or ventricular fibrillation (VF), or both VT and VF, for example) and supraventricular tachyarrhythmia. In some examples, the controller circuit 420 enables the rhythm discrimination module 440 when the controller circuit 420 detects that the detected sudden rate increase is sustained for a specified period of time. The specified period of time may be measured in seconds (e.g., ten seconds) or it may be measured in heartbeats. As an illustrative example, the controller circuit 420 detects that a sudden rate increase is sustained if eight out of ten heartbeats are accelerated beats. In some examples, the controller circuit 420 enables the rhythm discrimination module 440 when the controller circuit 420 detects that the ventricular rate exceeds the atrial rate by a specified rate difference threshold and that this ventricular rate is sustained for a specified period of time. Again, the controller circuit 420 may measure the specified period of time in seconds or in heartbeats. In some examples, the controller circuit 420 enables the rhythm discrimination module 440 when either the controller circuit 420 detects that both the sudden rate increase or the ventricular rate that exceeds the atrial rate are sustained for a specified period of time.

The rhythm discrimination module 440 typically discriminates between ventricular tachyarrhythmia and supraventricular tachyarrhythmia by performing different techniques than are performed by the detection module 435. In this way the tachyarrhythmia detection module 435 can be configured to increase the sensitivity of a detection device and the rhythm discrimination module 440 can be configured to increase the specificity of a detection device.

Sensitivity generally refers to the ability of the detection scheme to effectively detect an abnormal heart rhythm (e.g., VT/VF) that the physician desires the cardiac rhythm management device to treat. The sensitivity can be expressed as follows:

Sensitivity=True Positives/(True Positives+False Negatives).

Specificity generally refers to the ability of the detection scheme to avoid improperly treating rhythms (e.g., sinus tachycardia) that the physician determines that the device should not treat. The specificity can be expressed as follows:

Specificity=True Negatives/(True Negatives+False Positives).

For example, if the rhythm to be detected is VT/VF, then a true positive would occur when a particular rhythm is VT/VF and the detection algorithm correctly declares it as VT/VF. A false negative would occur when the rhythm is VT/VF and the detection algorithm erroneously declares it as not VT/VF. A false positive would occur when the rhythm is anything but VT/VF (e.g., normal sinus rhythm (NSR), sinus tachycardia, atrial fibrillation, atrial flutter, electrical noise, e.g., due to mypotentials, electromagnetic interference (EMI), a loose set screw for a leadwire, a broken leadwire, etc.) and the detection algorithm erroneously declares it as VT/VF. A true negative would occur when the rhythm is anything but VT/VF (e.g., normal sinus rhythm (NSR), sinus tachycardia, atrial fibrillation, atrial flutter, electrical noise, e.g., due to mypotentials, electromagnetic interference (EMI), a loose set screw for a leadwire, a broken leadwire, etc.) and the detection algorithm correctly declares it as not VT/VF.

In some examples, the rhythm discrimination module 440 performs a rhythm discrimination method that includes recurrently updating an average ventricular contraction interval (V-V interval) and determining that an average ventricular contraction rate exceeds an average atrial contraction rate by more than a specified rate threshold value. This differs from the atrial/ventricular rate detection performed by the tachyarrhythmia detection module 435 in that averages of the atrial and ventricular rate are used to confirm the tachyarrhythmia and discriminate from supraventricular tachyarrhythmia. Descriptions of systems and methods for classifying detected tachycardia based on average atrial and ventricular rates calculated from selected atrial and ventricular intervals is found in co-pending U.S. patent application Ser. No. 11/054,726, Elahi et al., entitled, "Method and Apparatus for Rate Accuracy Enhancement in Ventricular Tachycardia Detection," filed Feb. 10, 2005, which is incorporated herein by reference.

In some examples, the controller circuit includes a memory and the rhythm discrimination module 440 performs a morphology comparison of a sensed cardiac signal to a template of a known morphology (such as ventricular tachyarrhythmia or supraventricular tachyarrhythmia) stored in memory. For example, a template can be created for a patient using a CRM by providing electrical energy pulses to the supraventricular region of the patient's heart. The resulting cardiac complexes are then sensed and used to create a template for use in a morphology-based cardiac classification algorithm for classifying cardiac complexes as either VT or SVT. Systems and methods of creating templates for a morphology-based algorithm are described in Hsu, U.S. Pat. No. 6,889,081, entitled "Classification of Supraventricular and Ventricular Cardiac Rhythms Using Cross Channel Timing Algorithm," filed Jul. 23, 2002, which is incorporated herein by reference.

In another example, a template is generated from a snapshot representative of one of the patient's normal supra-ventricular conducted beats. Cardiac signals are sensed from pacing leads (rate channel) and shock leads (shock channel). A fiducial point is determined from the signals sensed on the rate channels and is used to align signals sensed on the shock channels. A template for a patient is generated using the aligned shock channel signals. The template is representative of one of the patient's normal supra-ventricular conducted beats. Subsequently detected beats are then used to confirm that the generated template is representative of one of the patient's normal supra-ventricular conducted beats. Systems and methods for generating templates using a snapshot of the patient's normal supra-ventricular conducted beats are described in Kim et al., U.S. Pat. No. 6,708,058, entitled "Normal Cardiac Rhythm Template Generation System and Method," filed Apr. 30, 2001, which is incorporated herein by reference.

In another example, a template of a patient's supraventricular rhythm is generated from characterizations performed while the heart is being paced. During the characterization, various pacing parameters are modified and the patient's supraventricular rhythm is characterized while the pacing parameters are modified. Systems and methods for generating a template to represent a patient's supraventricular rhythm are described in Bocek et al., U.S. Pat. No. 6,889,079, entitled "Method and System for Characterizing Supraventricular Rhythm During Cardiac Pacing," filed Apr. 12, 2002, which is incorporated herein by reference.

In some examples, the rhythm discrimination module 440 performs a rhythm discrimination method that includes determining that a specified number of atrial rate intervals measured over a consecutive number of heart beats are shorter than an atrial fibrillation rate threshold interval. In an example, at initiation of ventricular tachyarrhythmia, each atrial interval is classified as faster or slower than the atrial fibrillation rate threshold interval. When 6 of the last 10 intervals are classified as faster than the atrial fibrillation rate threshold interval, the device declares atrial fibrillation present.

In some examples, the rhythm discrimination module 440 performs a rhythm discrimination method that includes assessing stability of the ventricular rhythm. In an example, the stability is assessed by measuring the degree of variability of R-R intervals during the tachycardia episode. The current average difference between R-R intervals is compared to a programmed stability threshold and a "shock if unstable" threshold. If the average difference is greater than the programmed thresholds, the rhythm is declared unstable. Descriptions of advanced methods and systems to detect abnormal heart rhythms including determining that a specified number of atrial rate intervals measured over a consecutive number of heart beats are shorter than an atrial fibrillation rate threshold interval and assessing the stability of the ventricular rhythm are found in Gilkerson et al., U.S. Pat. No. 6,493,579, entitled "System and Method for Detection Enhancement Programming," filed Aug. 20, 1999, which is incorporated herein by reference.

The stability can be assessed by determining whether the ventricular rhythm is unstable using a measure of variability of ventricular time intervals, or the stability can be assessed from the variability of the rate in combination with measurements of other physiologic measurements, such as a hemodynamic pressure sensor for example.

In some examples, the rhythm discrimination module 440 uses a combination of morphology discrimination and rhythm discrimination to classify rhythms. In an example, the rhythm discrimination module may perform a morphology discrimination if a conflict among initial rhythm discriminators exists. Additional discrimination procedures can be used to enhance rhythm discrimination from additional information available in the system 400. For example, CRM devices often include a number of sensors that are used for diagnostic or therapeutic purposes. Sensor information acquired from such sensor components may be used with rhythm classification. Systems and methods for classifying cardiac rhythms by blending rhythm discriminators are described in Kim et al., U.S. patent application Ser. No. 11/089,185, entitled, "Blending Cardiac Rhythm Detection Processes," filed Mar. 24, 2005, which is incorporated herein by reference.

In some examples, multiple morphology templates are used in conjunction with rate discrimination. In an example, a morphology template for rest and a morphology template for exercise are used in conjunction with heart rate to classify rhythms. In a further example, a patient's metabolic need provides further information for such a classification. Systems and methods that use multiple morphology templates to discriminate between rhythms are found in Schwartz et al, U.S. Pat Appl. Pub. No. 20040093035, filed Nov. 8, 2002, which is incorporated herein by reference.

Once it determined that the tachyarrhythmia is ventricular tachyarrhythmia and not supraventricular tachyarrhythmia, some CFM devices treat the ventricular tachyarrhythmia. In some examples, the IMD 405 includes a therapy circuit coupled to the controller circuit 420. The therapy circuit delivers anti-tachyarrhythmia therapy when the rhythm discrimination module detects ventricular tachyarrhythmia.

In some examples, the IMD 405 is configurable to deliver anti-tachyarrhythmia therapy in the ventricle when the rhythm discrimination module 440 detects a slow ventricular tachyarrhythmia. This ventricular anti-tachyarrhythmia therapy can be selectively programmed by a physician to deliver either ventricular anti-tachycardia pacing (ATP) or ventricular defibrillation/cardioversion shocks, or a combination of both. In some examples, the rhythm discrimination module 440 can be configured to discriminate between normal sinus tachycardia and atrial tachyarrhythmias, such as by comparing the sensed atrial rate to an atrial tachyarrhythmia rate threshold that the physician programs to be above the patient's maximum sinus rate. In some examples, the IMD's 405 atrial anti-tachyarrhythmia therapy can be selectively programmed by the physician to deliver either atrial ATP or atrial defibrillation/cardioversion shocks or a combination of both in response to detection of an atrial tachyarrhythmia.

Anti-tachyarrhythmia therapy can result in perceived discomfort or acceleration of the tachyarrhythmia to higher rates that are poorly tolerated by the patient. For this reason, optimal therapy may be to withhold device therapy for slow tachyarrhythmias for which the patient has acceptable hemodynamic response. In some examples, atrial and/or ventricular therapy is programmable to be enabled only after evidence of hemodynamic compromise, such as by blood pressure falling below a physician programmable threshold as measured by an implantable pressure sensor for example. If a patient tolerates the presence of slow tachyarrhythmia for a period of time, device therapy may be delayed to allow the rhythm to self-terminate or to allow pharmacological interventions to be applied. Atrial and/or ventricular therapy may be programmed to activate following a physician programmable sustained duration of the slow VT (e.g. in a range of minutes to several hours).

ATP is implemented by providing one or more bursts of pacing pulses in one or more atria for atrial therapy, and one or more ventricles for ventricular therapy. The therapy may include programmable sequences of bursts with programmable amplitude, width, length, pacing interval, and coupling interval (time from a sensed beat of the tachycardia to the initial pulse in a burst). A ramp feature may be programmed that progressively shortens the pacing interval during each burst. A scan feature may be programmed to progressively that shortens the pacing interval from one burst to the next. Ramp and scan features may be programmed in combination. Pacing interval and coupling interval may be programmed to be adaptive to the sensed rate of the tachyarrhythmia. The physician may program multiple anti-tachycardia pacing sequences to be applied consecutively to a single tachyarrhythmia. If multiple bursts are programmed, redetection is applied after each burst to determine if the therapy has converted the tachyarrhythmia, or has resulted in acceleration of the arrhythmia to a higher rate, e.g. into a rate zone for which other therapy has been programmed. A programmable timeout may be provided to limit the total duration of ATP for a given episode of tachyarrhythmia. After all programmed ATP is delivered or the timeout is reached, ATP is exhausted for the episode. If both shock and ATP therapies are programmed, ATP is delivered first to minimize patient discomfort.

Ventricular or atrial shock therapy consists of delivery of one or more shocks of programmed energy levels. If multiple-shocks are programmed, successive shocks are normally constrained to have the same or increased energy level. If multiple shocks are programmed, redetection is applied after each burst to determine if the therapy has converted the tachyarrhythmia, or has resulted in acceleration of the arrhythmia to a higher rate, e.g. into a rate zone for which other therapy has been programmed. Shocks are normally delivered synchronously with a sensed depolarization of the ventricle. Atrial shocks are frequently constrained to be delivered only on intervals longer than a predetermined or computed minimum ventricular interval, to avoid ventricular pro-arrhythmia due to shock delivery on the ventricular vulnerable period. Before each shock, the defibrillator typically requires several seconds to charge internal energy storage capacitors to the programmed energy for that shock. Ventricular shocks may be programmed to be committed or uncommitted. For committed shocks, shock delivery takes place at the end of charging without regard to the patient's sense rate at the time charging completes place. For uncommitted shocks, the shock is withheld if the patient's rate is not found to be high at the end of charging, and redetection follows. After all programmed shocks have been delivered, shock therapy is exhausted for the episode.

Figure 6:
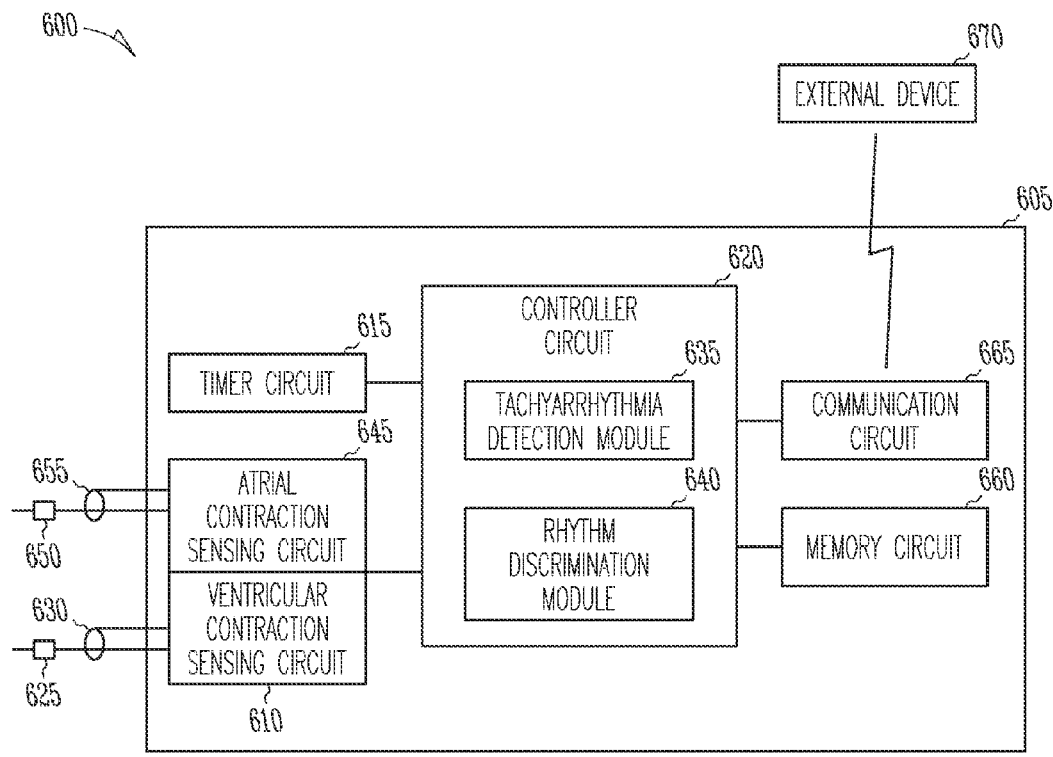
FIG. 6 shows another example of portions of a system that detects tachyarrhythmia.

FIG. 6 shows another example of a system 600 that detects tachyarrhythmia, including detecting tachyarrhythmia at rates below typical detection cutoff rates. The system 600 includes an IMD 605 and an external device 670. The IMD 605 in turn includes a ventricular contraction sensing circuit 610, an atrial contraction sensing circuit 645, a timer circuit 615, and a controller circuit 620. The controller circuit 620 includes a tachyarrhythmia detection module 635 and a rhythm discrimination module 640. The ventricular contraction sensing circuit 610 provides a ventricular contraction signal sensed through lead tip electrode 625 and lead ring electrode 630. The atrial contraction sensing circuit 645 provides an atrial contraction signal sensed through lead tip electrode 650 and lead ring electrode 655.

The system 600 includes a memory circuit 660 coupled to the controller circuit 620. In some examples, when the rhythm discrimination module 640 identifies an episode of tachyarrhythmia such as ventricular tachyarrhythmia or supraventricular tachyarrhythmia, the controller circuit 620 stores a digitized representation of the episode in the memory circuit 660. The digitized representation of the episode is obtained using sampling circuits to sample the electrical cardiac signals sensed by the sensing circuits 610, 645. In some examples, the controller circuit 620 stores episodes of ventricular tachyarrhythmia in a first area of memory and episodes of supraventricular tachyarrhythmia in a second area of memory, where "area of memory" refers to memory locations defined by a range of addresses.

It should be noted that the previously mentioned examples are capable of detecting tachyarrhythmia without first comparing a heart rate to a fixed tachyarrhythmia detection threshold rate or set of threshold rates (i.e., rate zones). These fixed rates are sometimes programmable. Some examples of these tachyarrhythmia rates include 140 beats per minute (bpm), 160 bpm, and 180 bpm. Because the examples do not require a comparison to a fixed tachyarrhythmia rate, tachyarrhythmia occurring below these rates can be detected. In addition, this allows detection of tachyarrhythmia at rates below a maximum pace rate.

However, after tachyarrhythmia detection, a comparison to these rates can provide information to a clinician that a patient is experiencing slow tachyarrhythmia. In some examples, the controller circuit 620 deems an episode of tachyarrhythmia as an episode of slow tachyarrhythmia when the tachyarrhythmia occurs at a ventricular rate less than a specified tachyarrhythmia detection rate. At least one digitized representation of an episode of slow tachyarrhythmia can be stored by the controller circuit 620 in the memory circuit 660. In some examples, a plurality of slow tachyarrhythmia episode representations are stored in the memory circuit 660 and the controller circuit 620 overwrites the oldest stored slow tachyarrhythmia episode representation with the most recent episode representation when memory storage available for slow tachyarrhythmia episode representations is full.

In some examples, the IMD 605 further includes a communication circuit 665 and the controller circuit 620 wirelessly communicates information related to a detected slow tachyarrhythmia to the external device 670. In some examples, the external device 670 is part of, or in communication-with, a computer network such as a hospital computer network or the internet. In some examples, the external device 670 is in communication with a mobile telephone network. In some examples, the external device is a repeater that communicates wirelessly with the IMD and with a third device in communication with a network, such as a computer network or mobile telephone network.

The controller circuit 620 communicates an indication of a detected slow tachyarrhythmia to the external device 670. The indication can be the entire digitized representation for display on the external device 670 or another device connected to the network, or the indication can be an alarm on the external device 670. In some examples, the alarm includes a notification sent to a clinician or clinician's office over the computer network, such as by e-mail, or the alarm includes an indication on a web page. In some examples, the alarm includes an indication or notification sent to a medical device service center. In some examples, the IMD 605 includes a speaker and the indication of slow tachyarrhythmia is an audible alarm originating from the IMD 605.

Figure 7:
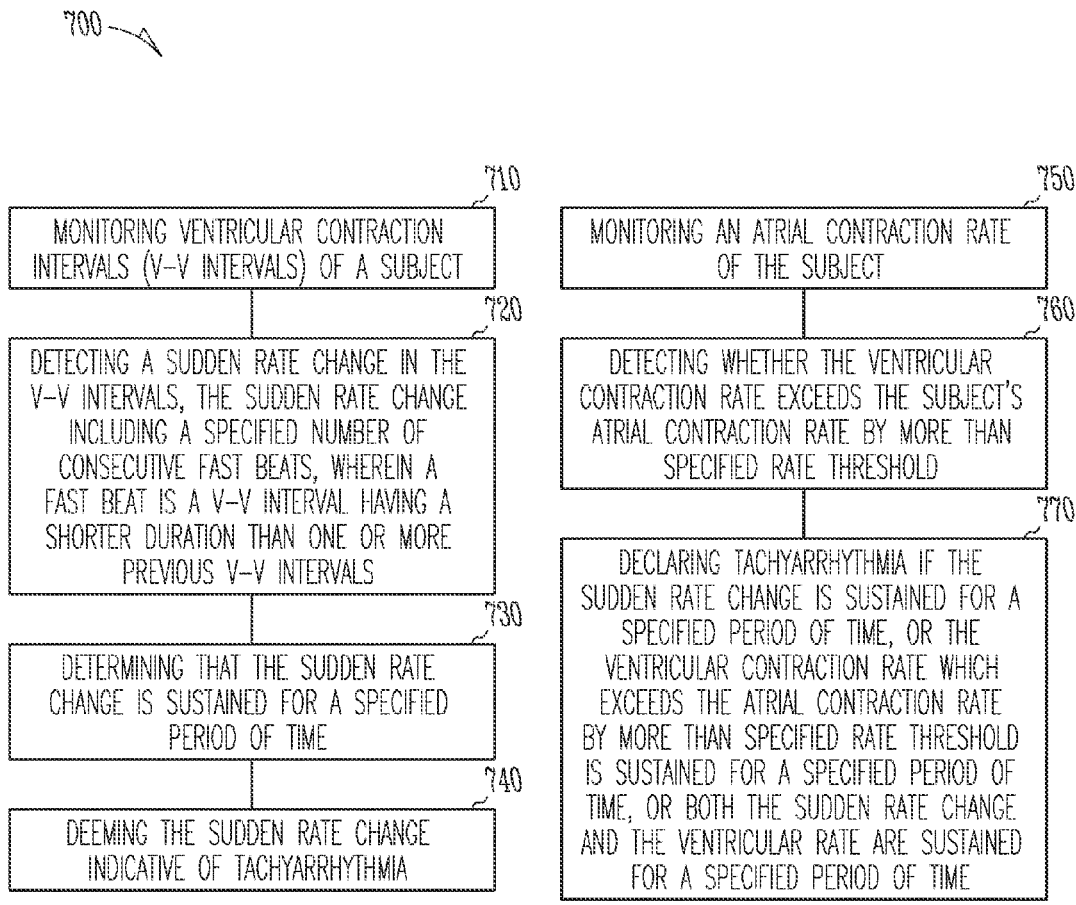
FIG. 7 is a block diagram of an example of a method of using an implantable medical device.

FIG. 7 is a block diagram of an example of a method 700 of using an IMD. At 710, ventricular contraction intervals (V-V intervals) of a subject are monitored. The intervals are monitored using cardiac signal sensing circuits. At 720, a sudden rate increase in the V-V intervals is detected. A sudden rate increase is declared by a specified number of consecutive accelerated beats. An accelerated beat typically is a V-V interval that is shorter than one or more previous V-V intervals by a threshold value.

In some examples of the method 700, detecting a sudden rate increase in the V-V intervals includes recurrently updating an average V-V interval and deeming that a current V-V interval indicates an accelerated beat if a difference between a last average V-V interval and the current V-V interval exceeds a specified percentage of the last average V-V interval. In some examples, recurrently updating an average V-V interval includes recurrently calculating an average V-V interval and a previously calculated average interval is given a greater weight in the calculation than a current rate interval. As an illustrative example, an average V-V interval, $V\text{-}V_{AVG}(n)$ is calculated by $$VV_{AVG}(n)=0.75*VV_{AVG}(n-1)+0.25*VV(n),$$

where VV(n) is the current rate interval. In some examples, the current V-V interval is excluded from an updated average V-V interval calculation if the current V-V interval indicates an accelerated beat. This prevents the accelerated beats from skewing the interval average toward the faster intervals if the sudden rate increase is sustained. In another example, the V-V interval that indicates an accelerated beat is not excluded from the updated average V-V interval until a sudden rate increase is declared, i.e., until a specified number of accelerated beats is detected. In an illustrative example, a current fast V-V interval is not excluded from the updated average until three consecutive accelerated beats are first detected.

In another example, once the specified number of accelerated beats needed to declare a sudden rate increase is detected, subsequent accelerated beats are used to define a temporary average V-V interval. The temporary average V-V interval is not updated in the same manner as the normal average V-V interval, but is used to identify accelerated beats after the average V-V interval converges to fast V-V intervals. For example, when a sudden rate increase is declared after three accelerated beats are detected, the current V-V interval and the normal average V-V interval are used to calculate a temporary average V-V interval. Subsequent V-V intervals shorter than the temporary average V-V interval are deemed to be accelerated beats.

At 730, whether the sudden rate increase is sustained for a specified period of time is determined. In some examples, determining that a sudden rate increase is sustained for a specified period of time includes determining that the accelerated beats are sustained over A of B ventricular time intervals, where A and B are integers, and $A \leq B$. For example, a sudden rate increase is determined to be sustained if 8 out of 10 ventricular time intervals are accelerated beats (i.e., A=8 and B=10). At 740, the sudden rate increase is deemed to indicate tachyarrhythmia if the sudden rate increase is sustained. The end of the tachyarrhythmia episode is detected if the fast time intervals are sustained over less than C of D V-V intervals, where C and D are integers, and C<D. For example, if an episode tachyarrhythmia is declared when 8 out of 10 ventricular time intervals are accelerated beats, the episode is declared to be over if 4 out of 10 ventricular time intervals are accelerated beats (i.e., C=4 and D=10).

According to some examples, the method 700 further includes, at 750, monitoring an atrial contraction rate (A-A intervals) of the subject. At 760, whether the ventricular contraction rate exceeds the subject's atrial contraction rate by more than specified rate threshold is detected. In some examples, the specified rate threshold is ten bpm. At 770, tachyarrhythmia is declared if the sudden rate increase is sustained for a specified period of time, or if the ventricular contraction rate, which exceeds the atrial contraction rate by more than specified rate threshold, is sustained for a specified period of time. Thus, in some examples tachyarrhythmia is detected only from a determination that the ventricular rate exceeds the atrial rate, and without detecting a sudden rate increase. Determining whether the high ventricular contraction rate is sustained can be based on time (e.g., tachyarrhythmia is declared if the rate is sustained for ten seconds) or it can be based on a number heart beats (e.g., tachyarrhythmia is declared if the ventricular rate interval is less than the atrial rate interval over ten ventricular contractions). In some examples, tachyarrhythmia is declared only if both the sudden rate increase and the ventricular rate are sustained for a specified period of time.

In some examples of the method 700, once tachyarrhythmia is detected, it is determined whether the tachyarrhythmia is ventricular tachyarrhythmia heart rhythms or supraventricular tachyarrhythmia heart rhythms. This is accomplished by using one or more advanced algorithms to discriminate the type of heart rhythm. These algorithms include determining that an average ventricular contraction rate exceeds an average atrial contraction rate by more than a specified rate threshold value, comparing a morphology of a sensed cardiac signal to a template morphology, determining that an atrial rate exceeds an atrial fibrillation rate threshold, and assessing the stability of the ventricular rhythm. In some examples, the stability is assessed by determining that the ventricular rhythm is unstable using a measure of variability of the ventricular time intervals. In some examples, the stability is assessed from variability of the intervals in combination a measurement of another physiologic parameter.

Because tachyarrhythmia is detected without first comparing a heart rate to a fixed tachyarrhythmia detection threshold rate or set of threshold rates, after tachyarrhythmia is detected a subsequent comparison to such a rate can determine if the patient experienced tachyarrhythmia at a relatively low heart rate for tachyarrhythmia, such as 140 bpm for example.

Therefore, in some examples of the method 700, an episode of tachyarrhythmia is deemed to be slow tachyarrhythmia when the ventricular rate is less than a specified tachyarrhythmia detection rate. In some examples, the method includes communicating an indication of slow tachyarrhythmia from the IMD to an external device.

In some examples, at least one digitized representation of an episode of slow tachyarrhythmia is stored in memory of the IMD. The digitized representations of the episode are obtained by sampling of electrical cardiac signals sensed using the IMD. These digitized representations can then be displayed. This allows a caregiver to read a sampled signal out from device memory and observe the episode of slow tachyarrhythmia at a subsequent patient visit. An indication in the IMD is communicated to an external device to alert the caregiver of the episode. In some examples, an external device located somewhere other than in a clinic, such as in a patient's home, can read out and communicate the sampled signal to the caregiver's location for display. This monitoring identifies those patients that experience slow tachyarrhythmia to a caregiver, allowing the caregiver to make adjustments to parameters of a CFM device or to adjust a patient's drug therapy.

In versions of the example, a plurality of episodes of slow tachyarrhythmia are stored in the IMD and, as the storage available for slow tachyarrhythmia episodes is filled, the oldest stored episode is overwritten with a most recent episode. In some examples, episodes of supraventricular tachyarrhythmia are also obtained and stored with episodes of slow tachyarrhythmia stored in a separate area of memory from the supraventricular episodes.

The accompanying drawings that form a part hereof, show by way of illustration, and not of limitation, specific examples in which the subject matter may be practiced. The examples illustrated are described in sufficient detail to enable those skilled in the art to practice the teachings disclosed herein. Other examples may be utilized and derived therefrom, such that structural and logical substitutions and changes may be made without departing from the scope of this disclosure. This Detailed Description, therefore, is not to be taken in a limiting sense, and the scope of various examples is defined only by the appended claims, along with the full range of equivalents to which such claims are entitled.

Such examples of the inventive subject matter may be referred to herein, individually and/or collectively, by the term "invention" merely for convenience and without intending to voluntarily limit the scope of this application to any single invention or inventive concept if more than one is in fact disclosed. Thus, although specific examples have been illustrated and described herein, it should be appreciated that any arrangement calculated to achieve the same purpose may be substituted for the specific examples shown. This disclosure is intended to cover any and all adaptations, or variations, or combinations of various examples. Combinations of the above examples, and other examples not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own.

What is claimed is:

1. A system comprising:
   an implantable medical device (IMD) comprising:
      a ventricular contraction sensing circuit operable to provide a sensed ventricular contraction signal;
      a timer circuit operable to provide a ventricular time interval between ventricular contractions;
      a controller circuit coupled to the timer circuit, the controller circuit operable to determine the ventricular contraction rate using the ventricular time interval, and wherein the controller circuit further includes a tachyarrhythmia detection module operable to:
      determine an average ventricular contraction interval;
      deem a current heartbeat as an accelerated beat if a difference between a last average ventricular contraction interval (V-V interval) and the current V-V interval is greater than a specified portion of the last average V-V interval;
      declare tachyarrhythmia, in response to detecting a sudden rate increase, without requiring comparing a ventricular rate or time interval to a respective tachyarrhythmia detection rate or time interval threshold, wherein a sudden rate increase is defined as a specified number of accelerated beats; and
      exclude an accelerated beat from a determination of the average V-V interval after the specified number of accelerated beats occurs.

2. The system of claim 1, wherein a sudden rate increase is defined as a specified number of consecutive accelerated beats.

3. The system of claim 1, further comprising an atrial contraction sensing circuit configured to sense a cardiac signal of an atrium of the heart, and wherein the controller circuit is operable to monitor a ventricular and an atrial contraction rate and the tachyarrhythmia detection module is operable to declare tachyarrhythmia when at least one of the ventricular contraction rate exceeds the atrial contraction rate by a specified rate threshold or when detecting a sudden rate increase.

4. The system of claim 3, wherein the tachyarrhythmia detection module is operable to declare tachyarrhythmia when both the ventricular contraction rate exceeds the atrial contraction rate by a specified rate threshold and a sudden rate increase is detected.

5. The system of claim 3, wherein the controller circuit further includes a rhythm discrimination module to discriminate between ventricular tachyarrhythmia and supraventricular tachyarrhythmia, wherein the controller circuit enables the rhythm discrimination module when the controller circuit detects that a) the sudden rate increase is sustained for a specified period of time, or b) the ventricular rate which exceeds the atrial rate by a specified rate threshold is sustained for a specified period of time, or c) both the sudden rate increase and the ventricular rate are sustained for a specified period of time.

6. The system of claim 5, further including a memory circuit coupled to the controller circuit, wherein at least one first area of the memory circuit is allocated to store a digitized representation of at least one episode of ventricular tachyarrhythmia and at least one second area of the memory circuit is allocated to store a digitized representation of at least one episode of supraventricular tachyarrhythmia.

7. The system of claim 5, wherein the rhythm discrimination module discriminates between ventricular tachyarrhythmia and supraventricular tachyarrhythmia by performing at least one of:
   (a) a rhythm discrimination method that includes recurrently updating an average ventricular contraction interval (V-V interval) and determining that an average ventricular contraction rate exceeds an average atrial contraction rate by more than a specified rate threshold value;
   (b) comparing a morphology of a sensed cardiac signal to a template morphology;
   (c) determining that a specified number of atrial rate intervals measured over a consecutive number of heart beats are shorter than an atrial fibrillation rate threshold interval; and
   (d) assessing the stability of the ventricular rhythm.

8. The system of claim 5, further including a therapy circuit coupled to the controller circuit, the therapy circuit operable to deliver anti-tachyarrhythmia therapy when the rhythm discrimination module detects ventricular tachyarrhythmia.

9. The system of claim 1, wherein the controller circuit is further operable to deem an episode of tachyarrhythmia as an episode of slow tachyarrhythmia when the ventricular rate is less than a lowest specified tachyarrhythmia detection rate.

10. The system of claim 9, wherein the specified tachyarrhythmia detection rate is 140 beats per minute (bpm).

11. The system of claim 9, wherein the specified tachyarrhythmia detection rate is less than a maximum pacing rate.

12. The system of claim 9, further including a memory circuit coupled to the controller circuit, the memory circuit to store a digitized representation of at least one episode of slow tachyarrhythmia.

13. The system of claim 12, wherein the memory circuit is operable to store a plurality of slow tachyarrhythmia episode representations and wherein the controller circuit overwrites the oldest stored slow tachyarrhythmia episode representation with the most recent episode representation when the storage available for slow tachyarrhythmia episode representations is full.

14. The system of claim 9, further including an external device and wherein the IMD further includes a communication circuit coupled to the controller circuit, wherein the controller circuit is operable to communicate information related to a detected slow tachyarrhythmia to the external device.

15. The system of claim 9, further including an external device coupled to a network, wherein the IMD further includes a communication circuit coupled to the controller circuit, and wherein the controller circuit is operable to communicate an indication of a detected slow tachyarrhythmia to the external device.

16. The system of claim 15, wherein the system includes means for providing an alarm indicating slow tachyarrhythmia.

17. The system of claim 1, wherein the tachyarrhythmia detection module is operable to declare tachyarrhythmia without comparing a ventricular rate or time interval to a respective tachyarrhythmia detection rate or time interval threshold, such that the tachyarrhythmia can be detected at a contraction rate greater than a maximum pacing rate as well as at a contraction rate less than the maximum pacing rate, wherein the maximum pacing rate is the greater of a maximum sensor rate and a maximum tracking rate of the IMD.

18. A system comprising:
   an implantable medical device (IMD) comprising:
      a ventricular contraction sensing circuit operable to provide a sensed ventricular contraction signal;
      an atrial contraction sensing circuit operable to provide a sensed atrial contraction signal;
      a timer circuit operable to provide a time interval between heart contractions; and
      a controller circuit coupled to the timer circuit, the controller circuit operable to monitor a ventricular and an atrial contraction rate, and wherein the controller circuit further includes a tachyarrhythmia detection module operable to:
         determine an average ventricular contraction interval;
         deem a current heartbeat as an accelerated beat if a difference between a last average ventricular contraction interval (V-V interval) and the current V-V interval is greater than a specified portion of the last average V-V interval;
         declare tachyarrhythmia, without requiring a comparison to a tachyarrhythmia detection rate threshold or time interval threshold, in response to at least one of the ventricular contraction rate exceeding the atrial contraction rate by a specified rate difference, or detecting a sudden ventricular rate change, wherein a sudden ventricular rate increase is defined as a specified number of accelerated beats;
         exclude an accelerated beat from a determination of the average V-V interval after the specified number of accelerated beats occurs; and
         to deem an episode of tachyarrhythmia as an episode of slow tachyarrhythmia when the ventricular rate is less than a lowest specified tachyarrhythmia detection rate.

19. The system of claim 18, wherein a sudden rate increase is defined as a specified number of consecutive accelerated beats, and wherein the tachyarrhythmia detection module is operable to deem a current heartbeat as an accelerated beat if a difference between a last average ventricular contraction interval (V-V interval) and the current V-V interval is greater than a specified percentage of the last average V-V interval.

20. The system of claim 18, wherein the specified tachyarrhythmia detection rate is 140 beats per minute (bpm).

21. The system of claim 18, further including a memory circuit coupled to the controller circuit, the memory circuit to store a digitized representation of at least one episode of slow tachyarrhythmia.

22. A method of using an implantable medical device (IMD) comprising:
   monitoring ventricular contraction intervals (V-V intervals) of a subject;
   determining an average ventricular contraction interval;
   deeming a current heartbeat as an accelerated beat if a difference between a last average ventricular contraction interval (V-V interval) and the current V-V interval is greater than a specified portion of the last average V-V interval;
   detecting a sudden rate increase in the V-V intervals without requiring comparing a ventricular rate or time interval to a respective tachyarrhythmia detection rate or time interval threshold, the sudden rate increase including a specified number of consecutive accelerated beats;
   excluding an accelerated beat from a determination of the average V-V interval after the specified number of consecutive accelerated beats occurs;
   determining that the sudden rate increase is sustained for a specified period of time; and
   deeming the sudden rate increase indicative of tachyarrhythmia.

23. The method of claim 22, further including:

monitoring an atrial contraction rate of the subject;

detecting whether the ventricular contraction rate exceeds the subject's atrial contraction rate by more than specified rate threshold; and declaring tachyarrhythmia if the sudden rate increase is sustained for a specified period of time or the ventricular contraction rate which exceeds the atrial contraction rate by more than specified rate threshold is sustained for a specified period of time, or both the sudden rate increase and the ventricular rate are sustained for a specified period of time.

24. The method of claim 22, further including discriminating between ventricular tachyarrhythmia heart rhythms and supraventricular tachyarrhythmia heart rhythms upon detecting that the sudden rate increase is sustained for a specified period of time, wherein discriminating between ventricular tachyarrhythmia and supraventricular tachyarrhythmia includes at least one of:

(a) determining that an average ventricular contraction rate exceeds an average atrial contraction rate by more than a specified rate threshold value;

(b) comparing a morphology of a sensed cardiac signal to a template morphology;

(c) determining that an atrial rate exceeds an atrial fibrillation rate threshold; and (d) assessing the stability of the ventricular rhythm.

25. The method of claim 22, wherein determining that the sudden rate increase is sustained for a specified period of time includes determining that the accelerated beats are sustained over A of B ventricular time intervals, where A and B are integers, and A<B.

26. The method of claim 22, further including deeming an end of tachyarrhythmia if the intervals are sustained over less than C of D V-V intervals, where C and D are integers, and C<D.

27. The method of claim 22, including recurrently calculating an average V-V interval, wherein a previous calculated average interval is given a greater weight than a current rate interval.

28. The method of claim 22, including deeming an episode of tachyarrhythmia as slow tachyarrhythmia when the ventricular rate is less than a specified tachyarrhythmia detection rate.

29. The method of claim 28, including communicating an indication of slow tachyarrhythmia to an external device.

30. The method of claim 28, including storing at least one episode of slow tachyarrhythmia in the IMD.

31. The method of claim 30, including:

storing a plurality of episodes of slow tachyarrhythmia in the IMD; and overwriting an oldest stored episode with a most recent episode when the storage available for slow tachyarrhythmia episodes is full.

32. The method of claim 30, including storing at least one episode of slow tachyarrhythmia detected as ventricular in origin in a first area of memory allocated to store a digitized representation of at least one episode of slow ventricular tachyarrhythmia, and storing at least one episode of supraventricular tachyarrhythmia detected as supraventricular in origin in a second area of memory allocated to store a digitized representation of at least one episode of supraventricular tachyarrhythmia.

33. The method of claim 22, further including delivering anti-tachyarrhythmia therapy when the sudden rate increase is deemed indicative of tachyarrhythmia.

* * * * *

UNITED STATES PATENT AND TRADEMARK OFFICE
CERTIFICATE OF CORRECTION

PATENT NO. : 7,702,384 B2
APPLICATION NO. : 11/301716
DATED : April 20, 2010
INVENTOR(S) : Jaeho Kim et al.

It is certified that error appears in the above-identified patent and that said Letters Patent is hereby corrected as shown below:

In column 17, line 35, in Claim 25, delete "$A<B$." and insert -- $A \leq B$. --, therefor.

Signed and Sealed this

Eighth Day of June, 2010

David J. Kappos
*Director of the United States Patent and Trademark Office*